US006554786B2

(12) United States Patent
Bennett

(10) Patent No.: US 6,554,786 B2
(45) Date of Patent: Apr. 29, 2003

(54) LYMPHOEDEMA BANDAGE

(75) Inventor: Paul Bennett, Swinford (GB)

(73) Assignee: Neopress Limited, Leicestershire (GB)

(*) Notice: Subject to any disclaimer, the term of this patent is extended or adjusted under 35 U.S.C. 154(b) by 0 days.

(21) Appl. No.: 10/000,861

(22) Filed: Oct. 24, 2001

(65) Prior Publication Data

US 2002/0062096 A1 May 23, 2002

(30) Foreign Application Priority Data

Nov. 21, 2000 (GB) .............................................. 0028256

(51) Int. Cl.7 .............................................. A61F 13/00
(52) U.S. Cl. .............................. 602/60; 602/75; 602/78
(58) Field of Search .............................. 602/41–43, 53, 602/60, 61, 63, 64, 75, 76, 78; 606/1, 201, 203, 215–217; 24/572.1, 573.09; 128/869–70, 876–77, 882

(56) References Cited

U.S. PATENT DOCUMENTS

| 1,970,042 | A | * | 8/1934 | Brathwaite | |
| 4,215,687 | A | * | 8/1980 | Shaw | |
| 4,832,010 | A | * | 5/1989 | Lerman | |
| 4,854,309 | A | * | 8/1989 | Elsey | |
| 5,254,122 | A |   | 10/1993 | Shaw | ........................ 606/201 |
| 5,372,575 | A | * | 12/1994 | Sebastian | |
| 5,653,244 | A | * | 8/1997 | Shaw | |

FOREIGN PATENT DOCUMENTS

| WO | WO 93/10727 | 6/1993 |
| WO | WO 97/46181 | 12/1997 |

OTHER PUBLICATIONS

British Search Report May 18, 2001, Appl. No. GB 0028256.6.

* cited by examiner

Primary Examiner—Nicholas D. Lucchesi
Assistant Examiner—Lalita M Hamilton
(74) Attorney, Agent, or Firm—McCracken & Frank

(57) ABSTRACT

A compression dressing for the treatment of lymphoedema can be applied directly by a patient without requiring the assistance of trained nursing staff. The dressing comprises a panel (1) of elastically stretchable material the outer surface of which has a loop pile structure. The panel is sized so that it can wrap once around a patient's limb with some overlap. A separable slide fastener is provided for connecting the panel to itself into a tubular support around the patient's limb, and comprises two rows of inter-engageable teeth mounted on two separate tapes (5,8). One tape (5) is secured to one longitudinal edge of the panel (1) and the other tape (8) is secured to an anchorage element which comprises a number of mutually spaced fabric tabs (11) each having on an under-surface hooks for anchoring the anchorage element (11) to the loop pile structure of the panel (1). The invention also provides a method of applying such a dressing to the limb of a patient.

20 Claims, 1 Drawing Sheet

LYMPHOEDEMA BANDAGE

BACKGROUND OF THE INVENTION

1. Field of the Invention

The invention provides a pressure dressing for the treatment of lymphoedema.

2. Background Art

Lymphoedema is a condition caused by obstruction of the lymphatic system in the body. It is the lymphatic system which is responsible for draining the spaces between cells of the body, ridding those spaces of excess fluid. The lymphatic system is a circulatory system entirely separate from that of the bloodstream. Where there is lymphatic obstruction there is a swelling of the associated patient limb, with the exudates being protein-rich, unlike non-lymphatic oedemas where the exudate is generally protein-depleted.

Chronic lymphoedema is a common side-effect of the surgical treatment for breast cancer in which lymph nodes are dissected as part of the surgical procedure. Additionally, radiotherapy which is used routinely in breast cancer treatment can damage the lymphatic function. The treatment of breast cancer is not however the sole cause of lymphoedema. There is an inherited condition, Milroy's Disease, which is responsible for poorly developing lymphatics. Obstruction of the lymphatic channels can also be caused by cancer, by scar tissue, by the historical removal of lymph nodes or by fibrosis caused by X-ray therapy.

Lymphoedema can occur in any of the limbs of a patient, although it is most common for it to be present in the arms as opposed to the legs. The recognized treatment is the application of pressure over the whole of the limb. The pressure expresses the lymphatic fluid from the inter-cellular spaces. Considerable pressure can be applied, so long as it is applied uniformly over the limb. As a generality, the accumulated lymphatic fluid in the limb protects the patient's blood vessels from collapse due to excessive pressure, so the patient's blood flow is not adversely affected by the use of a tight compression dressing.

It has been proposed to apply the necessary pressure on the limb by means of a compression dressing comprising an inflatable sleeve. The inflatable sleeve can however be applied only when the patient is lying prone, and the inflation mechanism and the means for monitoring the pressure applied render the device wholly non-portable. The usual treatment for lymphoedema is therefore not the use of such a sleeve but the process of bandaging the limb with a tightly wound elasticated bandage. That however is something which requires skill and experience, and cannot be done by the patient alone.

The object of this invention is to provide a compression dressing for the treatment of lymphoedema which can be applied safely and reliably by the patient unaided.

BRIEF SUMMARY OF THE INVENTION

The invention provides a compression dressing for the treatment of lymphoedema, comprising
- a panel of elastically stretchable material of a size sufficient to wrap once around a patient's limb with some overlap, the outer surface of the panel having a loop pile structure; and
- a separable slide fastener comprising two rows of inter-engageable teeth mounted on two separate tapes, one of the tapes being secured to one longitudinal edge of the panel and the other of the tapes being secured to an anchorage element which comprises a number of mutually spaced fabric tabs each having on an under surface hooks for anchoring the anchorage element to the loop pile structure of the panel.

The invention also provides a method of applying such a dressing to a limb, comprising measuring the circumference of the limb at a number of mutually spaced locations; using these measurements to anchor the said other of the tapes to the panel along a line corresponding to the desired degree of compression; connecting together a first end portion of the separable slide fastener; placing the connected end of the panel around the limb and closing the slide fastener to wrap the dressing around the limb with the desired degree of compression. Such a method can be carried out by the patient without nursing assistance, which is a great step forward over conventional bandage-wrapping techniques.

Lymphoedema is most commonly encountered in connection with the arms of patients, and for illustrative purposes only the remainder of this specification will make reference to arm dressings only. The reader will readily understand how the teachings can be modified to be pertinent to leg dressings.

The panel preferably has a cuff portion extending beyond the slide fastener tapes, to surround the hand of the patient. An oval thumb-hole is generally provided in this cuff portion, so that when the first end portion of the slide fastener is connected together so as to draw that cuff portion into a generally tubular configuration, the patient can insert his wrists through the tubular end with his thumb through the thumb-hole. The thumb-hole anchors the dressing at the wrist as the slide fastener is closed. Advantageously the ends of the cuff portion are themselves connectable together by the mating parts of a hook-and-pile fastener to maintain the cuff tight around the patient's hand. It has been suggested that a pressure pad may advantageously be provided, to locate across the patient's palm, to extend the pressure of the dressing to the palm as well as to the back of the hand.

The separable slide fastener is the type of fastener commonly available under the Trade Mark "ZIP" fastener, and is of the type where the two tapes, each carrying its own row of metal or plastic teeth, can be completely separated. A slide connection is generally provided at one end of the slide fastener for establishing initial inter-engagement between the teeth prior to drawing a slide along the two rows of teeth to draw all teeth into mutually locking inter-engagement.

The loop pile structure of the outer surface of the panel and the hooks of the under surface of the tabs of the anchorage element form the two elements of a conventional hook-and-pile fastening system which is commercially available under the Trade Mark "VELCRO". Preferably the loop pile structure is provided over the whole of the outer surface of the panel.

The panel is preferably of 2-way stretch material. Neoprene foam sheeting is very suitable, of the kind used in divers' wetsuits. Such material has to be perforated to make it permeable. The optimum thickness of a neoprene foam sheet can be determined by trial and error, and will be dependent on the quality of the rubber. Sheets of thickness 2 mm or 3 mm may be suitable, depending on the modulus of elasticity. Alternatively the panel may be made from a suitable elastic knitted or woven stretch material.

DETAILED DESCRIPTION OF THE INVENTION

Figure 1:
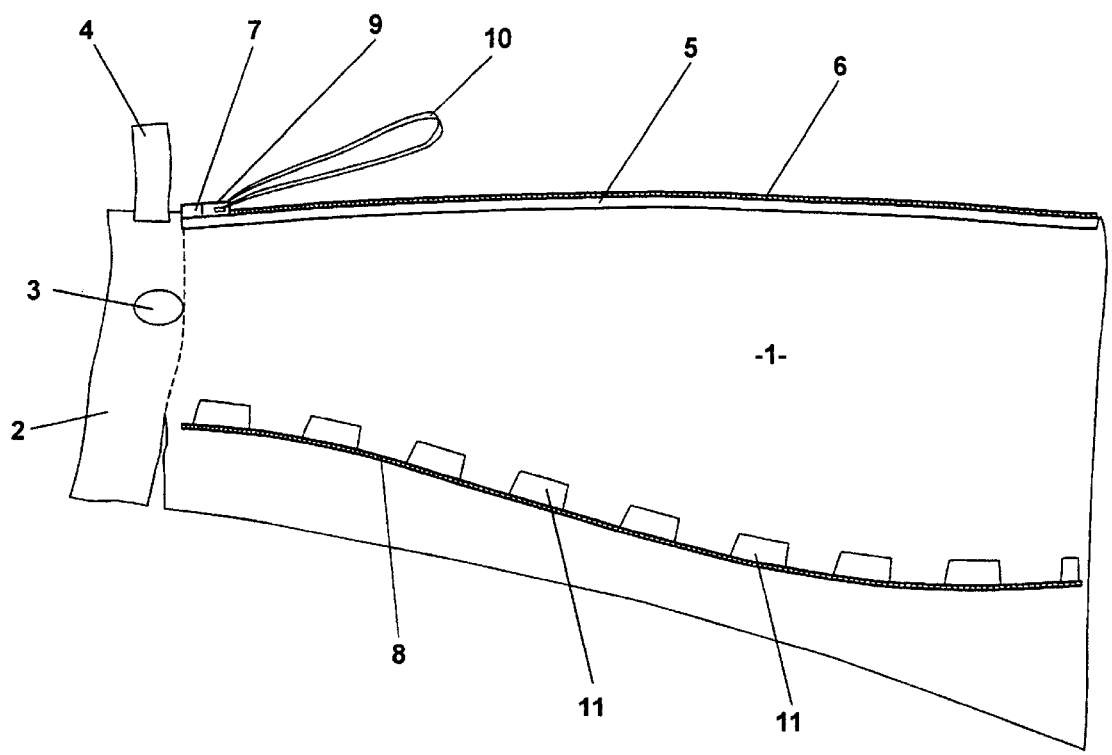
FIG. 1 is a plan view of a dressing according to the invention laid out flat.

In the drawings, the dressing comprises a panel 1 of a two-way stretch material with a high modulus of elasticity. High density foamed neoprene rubber is very suitable, although to avoid sweating of the limb when dressed the rubber should be perforated to make it breathable. 1 mm diameter perforations at approximately 1 cm spacings are adequate to establish that breathability. The underside of the panel (the inner surface in use) is preferably clad with a woven or knitted stretch fabric of natural or man-made fibers for comfort. The top side as viewed in FIG. 1 (the outer surface in use) is clad with a material having a loop pile structure to provide the loop compression of a VELCRO™ fastening.

Figure 2:
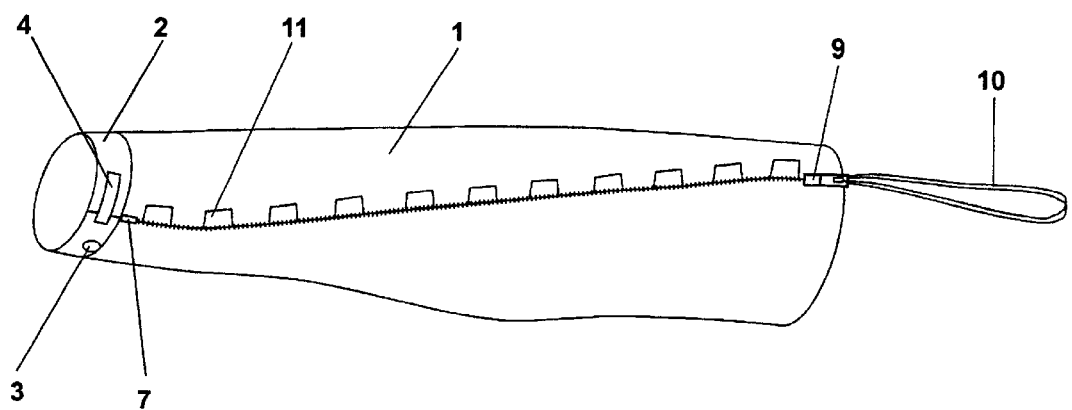
FIG. 2 is a perspective view of a dressing when drawn into a tube.

The panel 1 is edged along one end by a conjoined cuff element 2 of similar construction, with a thumb-hole 3 formed therein. A tab 4 has a hook formation on an underside, forming the hook component of a VELCRO™ fastening for when the dressing is wrapped around a patient's arm (FIG. 2).

Along one longitudinal edge of the panel 1 is sewn one half of a separable slide fastener of the type marketed under the Trade Mark ZIP. Such a fastener has teeth 6 formed on a mounting tape 5. The tape 5 is sewn to the neoprene panel 1. An engagement slide 7 for establishment of the initial connection between the two halves 5 and 8 of the slide fastener is located at the cuff end. Also shown at 9 is the slide of the slide fastener, from which extends a loop of ribbon 10 for easy pulling of the slide.

The other half 8 of the slide fastener is not permanently attached to the panel 1 at all. It is sewn to a continuous edge of a tape of hooked material which forms the hook component of a VELCRO™ hook and pile fastening. Apart from its continuous edge, the hooked tape is cut into a crenellated formation so that a plurality of mutually spaced anchorage tabs 11 are formed along the length of the slide fastener half 8. The reason for the crenellation is twofold. In the first place the longitudinal division of the hooked tape into discrete spaced anchorage portions or tabs 11 gives flexibility to the anchorage of the tape. When laid along a prescribed line on the panel 1, that line can be straight or cured. In the second place two such crenellated formations can be cut from a single length of parallel-sided hooked tape, so as to eliminate material wastage.

In use, the patient's arm is measured in a number of places: around the wrist, forearm, below and above the elbow and at the bicep and top of the upper arm. Those measurements are transferred to the panel 1, for example being marked on the panel with ball-point pen. Then the separable half 8 of the slide fastener is laid along a line parallel to a line joining those markings, to define a final dressing of slightly smaller circumference to the arm circumference at the various points measured. The spacing between the markings and the final line of the fastener half 8 can be chosen at will to define the degree of compression applied by the dressing. The fastener half 8 is held firmly in place by the hook and pile anchorage of the tabs 11.

Finally the cuff portion 2 is formed into a tube, the engagement slide 7 engaged with the other half of the slide fastener and the slide 9 moves for one or two centimeters to lock the two halves of the fastener together. Then the patient can insert his or her wrist with the thumb extending through the thumb-hole 3 and draw on the ribbon 10 to pull the slide 9 and close the panel 1 around the limb in compression. As the lymphoedema retracts, the hooked tabs 11 can be repositioned so as to decrease the nominal diameter of the tube created by the dressing, and maintain an optimum pressure on the limb.

The cuff 2 may be formed as one piece with the panel 1 or may be formed as a separate piece and stitched to the remainder of the panel 1. The latter construction makes it easier to form the thumb-hole 3. The cuff 2 can then have loop pile material on both surfaces, the inner surface accepting a hooked pressure pad (not shown) for exerting pressure on the patient's palm. Alternatively if a pressure pad is to be used it may be a hooked pressure pad adhered to a small panel of loop pile material stitched onto the cuff 2, or may be inserted into a pocket formed in the cuff 2.

What is claimed is:

1. A compression dressing for the treatment of lymphoedema, comprising:
   a panel of elastically stretchable material of a size sufficient to wrap once around a patient's limb with some overlap, the outer surface of the panel having a loop pile structure; and
   a separable slider fastener comprising two rows of inter-engageable teeth mounted on two separate tapes, one of the tapes being secured to one longitudinal edge of the panel and the other of the tapes being secured to an anchorage element which comprises at least one member having on an under surface thereof hooks for anchoring the anchorage element to the loop pile structure of the panel.

2. A compression dressing according to claim 1, shaped and sized to wrap around a patient's forearm and upper arm.

3. A compression dressing according to claim 1, wherein the panel further comprises a cuff portion extending beyond the slide fastener tapes, to surround the hand of the patient.

4. A compression dressing according to claim 3, wherein the cuff portion incorporates an oval thumb-hole.

5. A compression dressing according to claim 3, wherein the ends of the cuff portion are connectable together by the mating parts of a hook-and-pile fastener to maintain the cuff tight around the patient's hand in use.

6. A compression dressing according to claim 3, further comprising a pressure pad, to locate across the patient's palm and thereby to extend the pressure of the dressing to the palm as well as to the back of the hand.

7. A compression dressing according to claim 1, wherein the panel is made of a two-way stretch material.

8. A compression dressing according to claim 7, wherein the panel is made of neoprene foam sheeting, perforated to make it air permeable.

9. A compression dressing according to claim 8, wherein the neoprene foam sheeting is of thickness from 2 mm to 3 mm.

10. A method of applying to a limb of a patient a compression dressing according to claim 1, comprising measuring the circumference of the limb at a number of mutually spaced locations; using these measurements to anchor the said other of the tapes to the panel along a line corresponding to the desired degree of compression; connecting together a first end portion of the separable slide fastener; placing the connected end of the panel around the limb and closing the slider fastener to wrap the dressing around the limb with the desired degree of compression.

11. A compression dressing for the treatment of lymphoedema, comprising:
   a panel of elastically stretchable material of a size sufficient to wrap once around a patient's limb with some overlap, the outer surface of the pane having a loop pile structure; and a separable slide fastener comprising two rows of inter-engageable teeth mounted on two separate tapes, one of the tapes being secured to one longitudinal edge of the panel and the other of the tapes being secured to an anchorage element which comprises a number of mutually spaced fabric tabs each having on an under surface hooks for anchoring the anchorage element to the loop pile structure of the panel.

12. A compression dressing according to claim 11, shaped and sized to wrap around a patient's forearm and upper arm.

13. A compression dressing according to claim 11, wherein the panel further comprises a cuff portion extending beyond the slide fastener tapes, to surround the hand of the patient.

14. A compression dressing according to claim 13, wherein the cuff portion incorporates an oval thumb-hole.

15. A compression dressing according to claim 13, wherein the ends of the cuff portion are connectable together by the mating parts of a hook-and-pile fastener to maintain the cuff tight around a patient's hand in use.

16. A compression dressing according to claim 13, further comprising a pressure pad, to locate across the patient's palm and thereby to extend the pressure of the dressing to the palm as well as to the back of the hand.

17. A compression dressing according to claim 11, wherein the panel is made of a two-way stretch material.

18. A compression dressing according to claim 17, wherein the panel is made of neoprene foam sheeting, perforated to make it air permeable.

19. A compression dressing according to claim 18, wherein the neoprene foam sheeting is of thickness from 2 mm to 3 mm.

20. A method of applying to a limb of a patient a compression dressing according to claim 11, comprising measuring the circumference of the limb at a number of mutually spaced locations; using these measurements to anchor the said other of the tapes to the panel along a line corresponding to the desired degree of compression; connecting together a first end portion of the separable slide fastener; placing the connected end of the panel around the limb and closing the slide fastener to wrap the dressing around the limb with the desired degree of compression.

* * * * *